US010401334B2

(12) United States Patent
Ohashi et al.

(10) Patent No.: US 10,401,334 B2
(45) Date of Patent: Sep. 3, 2019

(54) CONTROL SYSTEM AND PROGRAM FOR LIQUID CHROMATOGRAPH

(75) Inventors: Hiroshi Ohashi, Otsu (JP); Tadayuki Yamaguchi, Kawasaki (JP); Hidetoshi Terada, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 1342 days.

(21) Appl. No.: 13/549,699

(22) Filed: Jul. 16, 2012

(65) Prior Publication Data
US 2013/0018598 A1 Jan. 17, 2013

(30) Foreign Application Priority Data

Jul. 15, 2011 (JP) .................................. 2011-157131
Jul. 15, 2011 (JP) .................................. 2011-157132

(51) Int. Cl.
*G01N 30/34* (2006.01)
*G01N 30/86* (2006.01)
(Continued)

(52) U.S. Cl.
CPC ......... *G01N 30/34* (2013.01); *G01N 30/8693* (2013.01); *G01N 30/8696* (2013.01);
(Continued)

(58) Field of Classification Search
CPC ...... B01D 15/203; B01D 15/20; G01N 30/86; G01N 30/8696; G01N 30/8693;
(Continued)

(56) References Cited

U.S. PATENT DOCUMENTS 4,239,623 A * 12/1980 Schrenker .................... 210/96.1
4,357,668 A * 11/1982 Schwartz et al. ............... 702/32
(Continued)

FOREIGN PATENT DOCUMENTS

| AP | 2102 A | 2/2010 |
| JP | 2005-127814 A | 5/2005 |
| WO | 02/46739 A1 | 6/2002 |

OTHER PUBLICATIONS

Steiner et al. Automated method development utilizing software-based optimization and direct instrument control. Dionex (2010), pp. 1-6.*
(Continued)

*Primary Examiner* — Katherine Zalasky
(74) *Attorney, Agent, or Firm* — Westerman, Hattori, Daniels & Adrian, LLP

(57) ABSTRACT

The present invention aims at reducing the time required for a series of analyses in the sequential performance of gradient analyses under a variety of conditions. To this end, in a control apparatus for controlling the operation of a liquid chromatograph having a gradient analysis function in which a mobile phase composed of a plurality of mixed solvents is used and a chromatograph analysis is performed while the mixture ratio of the solvents is temporally changed, the liquid chromatograph is controlled so as to continuously change the mixture ratio of the solvents from an initial mixture ratio to a final mixture ratio when performing a sample analysis; and as to perform, before the sample analysis, a preparatory liquid supply in which the mixture ratio of the solvents is continuously changed from the initial mixture ratio to the final mixture ratio at a rate higher than that in the sample analysis.

9 Claims, 11 Drawing Sheets

(51) Int. Cl.
*G01N 30/88* (2006.01)
*B01D 15/20* (2006.01)

(52) U.S. Cl.
CPC ........ *B01D 15/203* (2013.01); *G01N 30/8651* (2013.01); *G01N 2030/8804* (2013.01)

(58) Field of Classification Search
CPC ........... G01N 30/8651; G01N 30/8658; G01N 30/50; G01N 30/88; G01N 30/28; G01N 2030/889; G01N 2030/8809; G01N 2030/8804
See application file for complete search history.

(56) References Cited

U.S. PATENT DOCUMENTS

| | | | | |
|---|---|---|---|---|
| 4,969,993 A | * | 11/1990 | Nash et al. | 210/198.2 |
| 5,670,054 A | * | 9/1997 | Kibbey et al. | 210/656 |
| 6,344,172 B1 | * | 2/2002 | Afeyan et al. | 422/70 |
| 6,691,053 B2 | * | 2/2004 | Quimby et al. | 702/89 |
| 2002/0010566 A1 | * | 1/2002 | Chester et al. | 703/2 |
| 2002/0107652 A1 | * | 8/2002 | Andrews et al. | 702/104 |
| 2004/0253147 A1 | * | 12/2004 | Golushko | 422/71 |
| 2006/0054543 A1 | * | 3/2006 | Petro et al. | 210/198.2 |

OTHER PUBLICATIONS

Cazes, Jack. Encyclopedia of Chromatography, "Gradient elution: Overview." Copyright 2001 by Marcel Decker, pp. 390-392.*
Office Action dated Feb. 25, 2014, issued in Chinese Patent Application No. 201210245809.1 with Partial English Translation (6 pages).
Office Action dated Aug. 18, 2017, issued in counterpart Indian Patent Application No. 2819/CHE/2012 (6 pages; w/ English translation).

* cited by examiner

Fig. 3A

| ANALYSIS NUMBER | SAMPLE NAME | INJECTION AMOUNT | METHOD FILE NAME | DATA FILE NAME | ... |
|---|---|---|---|---|---|
| 1 | — | — | METHOD 1 | DATA 1 | ... |
| 2 | SAMPLE 1 | 10 | METHOD 1 | DATA 2 | ... |
| 3 | — | — | METHOD 2 | DATA 3 | ... |
| 4 | SAMPLE 1 | 10 | METHOD 2 | DATA 4 | ... |
| 5 | — | — | METHOD 3 | DATA 5 | ... |
| 6 | SAMPLE 1 | 10 | METHOD 3 | DATA 6 | ... |
| ⋮ | ⋮ | ⋮ | ⋮ | ⋮ | |

Fig. 3B

| ANALYSIS NUMBER | SAMPLE NAME | INJECTION AMOUNT | METHOD FILE NAME | DATA FILE NAME | ... |
|---|---|---|---|---|---|
| 1 | — | — | METHOD 1' | 20110706_XRODS_WATER_ACN_5_95 | ... |
| 2 | SAMPLE 1 | 10 | METHOD 1 | 20110706_XRODS_WATER_ACN_5_95 | ... |
| 3 | — | — | METHOD 2' | 20110706_XRODS_WATER_ACN_5_75 | ... |
| 4 | SAMPLE 1 | 10 | METHOD 2 | 20110706_XRODS_WATER_ACN_5_75 | ... |
| 5 | — | — | METHOD 3' | 20110706_XRODS_WATER_ACN_5_55 | ... |
| 6 | SAMPLE 1 | 10 | METHOD 3 | 20110706_XRODS_WATER_ACN_5_55 | ... |
| ⋮ | ⋮ | ⋮ | ⋮ | ⋮ | |

Fig. 12A

| ANALYSIS NUMBER | SAMPLE NAME | INJECTION AMOUNT | METHOD FILE NAME | DATA FILE NAME | ... |
|---|---|---|---|---|---|
| 1 | — | — | METHOD 1 | DATA 1 | ... |
| 2 | SAMPLE 1 | 10 | METHOD 1 | DATA 2 | ... |
| 3 | — | — | METHOD 2 | DATA 3 | ... |
| 4 | SAMPLE 1 | 10 | METHOD 2 | DATA 4 | ... |
| 5 | — | — | METHOD 3 | DATA 5 | ... |
| 6 | SAMPLE 1 | 10 | METHOD 3 | DATA 6 | ... |
| 7 | — | — | METHOD 4 | DATA 7 | ... |
| 8 | SAMPLE 1 | 10 | METHOD 4 | DATA 8 | ... |
| ⋮ | ⋮ | ⋮ | ⋮ | ⋮ | ... |

Fig. 12B

| ANALYSIS NUMBER | SAMPLE NAME | INJECTION AMOUNT | METHOD FILE NAME | DATA FILE NAME | ... |
|---|---|---|---|---|---|
| 1 | — | — | METHOD 1 | 20110706_XRODS_WATER_ACN_5_75 | ... |
| 2 | SAMPLE1 | 10 | METHOD 1 | 20110706_XRODS_WATER_ACN_5_75 | ... |
| 3 | SAMPLE1 | 10 | METHOD 2 | 20110706_XRODS_WATER_ACN_5_55 | ... |
| 4 | — | — | METHOD 3 | 20110706_XRODS_WATER_ACN_15_75 | ... |
| 5 | SAMPLE1 | 10 | METHOD 3 | 20110706_XRODS_WATER_ACN_15_75 | ... |
| 6 | SAMPLE1 | 10 | METHOD 4 | 20110706_XRODS_WATER_ACN_15_55 | ... |
| ⋮ | ⋮ | ⋮ | ⋮ | ⋮ | |

CONTROL SYSTEM AND PROGRAM FOR LIQUID CHROMATOGRAPH

TECHNICAL FIELD

The present invention relates to a control apparatus for controlling the operation of a liquid chromatograph, and a program used in the control apparatus.

BACKGROUND ART

A liquid chromatograph is composed of a plurality of units such as an auto sampler, a pump, and a column oven. The operation of each unit is controlled by means of the control signal from a control apparatus.

In recent years, a personal computer in which a control/process program has been installed is widely used as the control apparatus in such liquid chromatographs in order to generally control the analysis units and process the collected data. In such a control apparatus a schedule table is created before initiating an analysis so that multiple specimens can be continuously analyzed or other types of analysis can be automatically performed (for example, refer to JP-A 2005-127814).

FIG. 15 shows an example of a schedule table for a liquid chromatograph analysis. In this table, each row corresponds to an analysis. A row contains the information required to perform the analysis, such as the sample number, sample injection amount, method file name, data file name for storing the result of the analysis, and other information. A method file is a file in which the operation conditions (which will be hereinafter called an "analysis method") of each of the units composing the liquid chromatograph are defined. A variety of parameters, such as the kind of mobile phase, the kind of column used in the analysis, the flow rate of the pump, the temperature of the column oven during the analysis, and other information, are also contained in the file.

After such a schedule table is created, and when an initiation of an analysis is commanded, samples are sequentially selected and the analysis conditions are set in accordance with the schedule so that the multiple samples are automatically analyzed.

In such a liquid chromatograph, a sample is analyzed under various conditions, in some cases, in order to find the best analysis conditions for the sample. This operation is called "method scouting." In method scouting, the following operations are done: a user creates a number of different kinds of method files in advance in which the various parameters mentioned earlier are combined in various ways; the user specifies different method files in each row of a schedule table, as shown in FIG. 15; and the user instructs an initiation of the analysis with the same sample name and the sample injection amount for each row. Analyses are thereby performed sequentially under a variety of conditions in accordance with the description of the method file of each row. The chromatogram data resulting from the analyses are stored as one data file per analysis, and then saved in a memory unit such as a hard disk drive. The user refers to the chromatogram data stored in the memory unit to determine the analysis conditions under which the optimum analysis result was obtained in order to select the analysis method to be used for the sample.

One-known analysis method for a liquid chromatograph is a gradient solution sending method. In this method, solvents with different characteristics, such as water and organic solvents, are mixed, and a mobile phase liquid in which the mixture ratio of the solvents changes as time elapses is sent to a column. This method is particularly effective in adequately separating a sample composed of multiple components into the individual components.

In performing an analysis by using a gradient solution sending method (which will be hereinafter called a "gradient analysis"), a user sets a gradient profile such as that shown in FIG. 6 as an analysis parameter included in the method file. The gradient profile indicates the target values of the mobile phase composition over time from the initiation of an analysis. The example in FIG. 6 shows the profile of a gradient analysis in which the mixed liquid of solvent A and solvent B is used as the mobile phase and the mobile phase composition is expressed as the proportion of solvent B in the mixed liquid. A solvent that has a low elution capability (e.g. a highly polar solvent in the case of reverse mode) is used for solvent A. A solvent with a high elution capability (e.g. a low polar solvent in the case of reverse mode) is used for solvent B. At first, the amount of the solvent B is kept low until a predetermined period of time elapses from the injection of the sample at the point in time t0 (i.e. time t0 through t1). Consequently, the components contained in the sample are temporarily adsorbed in the column. The proportion of the solvent B increases in proportion to the time elapsed (time t1 through t2). As a result, the components are sequentially eluted from the column according to their characteristics (e.g. polarity). Subsequently, for a predetermined period of time (time t2 through t3), the proportion of solvent B is kept high so that the components remaining in the column are discharged from it. After that, the mobile phase composition returns to its initial state. This state is maintained for a predetermined period of time (time t3 through t4) so that the inside of the column is equilibrated.

Hereinafter, the process performed during the time t0 through t1 is called a sample introduction process. The process performed during the time t1 through t2 is called a gradient process. The process performed during the time t2 through t3 is called a washing process, and the one performed during the time t3 through t4 is called an equilibration process. In some cases, the sample introduction process may be omitted and the gradient process may be started simultaneously with the injection of a sample.

BACKGROUND ART DOCUMENT

Patent Document

[Patent Document 1] JP-A 2005-127814

DISCLOSURE OF THE INVENTION

Problems to be Solved by the Invention

As previously described, in a gradient analysis, a washing process is performed after a gradient process in order to wash the inside of a column, followed by an equilibration process for equilibrating the inside of the column. However, the retention time of each component in the first analysis may not be the same as that of the second or any subsequent analysis in a repeated, sequential performance of a gradient analysis of the same sample under the same conditions. For example, FIG. 16 shows overlapped chromatograms resulting from three gradient analyses of the same sample which have been sequentially performed under the same conditions. The chromatograms obtained in the second and third analyses (shown with heavy lines) are completely identical, whereas the peak appears at different times (i.e. different retention times) in the chromatogram obtained in the first analysis (shown with a thin line) and any other chromatograms.

Such a shift in retention times is caused by the fact that the equilibrated state of the column differs at the initiation of the first analysis from that of the second or subsequent analyses. Hence, in order to obtain an appropriate result from a gradient analysis, it is necessary to perform multiple analyses under the same conditions and use the data from the second analysis onward. In such cases, the second and subsequent analyses will be called a proper analysis, and the first analysis will be called a null analysis.

Accordingly, when the above-mentioned method scouting is performed with multiple analyses using a variety of gradient profiles, it is necessary to perform a null analysis using the same gradient profile as that of the proper analyses in advance of every proper analysis performed with each gradient profile. This causes problems as it requires a long time to complete the series of analyses.

Since a variety of analysis conditions are examined in method scouting, the number of analyses tends to be large. Consequently, the results of the analysis create numerous data files. This brings about another problem in that it is not possible to ascertain the conditions of the analysis with which the result has been obtained unless the data file is opened.

The present invention has been developed to solve the aforementioned problems. The first objective thereof is to provide a control apparatus for a liquid chromatograph capable of reducing the time required for a series of analyses in the case where gradient analyses with a variety of gradient profiles are sequentially performed. The second objective thereof is to provide a control apparatus for a liquid chromatograph with which the user can easily ascertain the conditions of the analysis just by looking at the name of the analysis result data file, no matter how many data files there are.

Means for Solving the Problems

To solve the aforementioned problems, the first aspect of the present invention provides a control apparatus for controlling an operation of a liquid chromatograph that has a gradient analysis function in which a chromatograph analysis is performed while a mixture ratio of a plurality of solvents composing a mobile phase is temporally changed, the control apparatus including:

a) an analysis controller for controlling the liquid chromatograph so as to continuously change the mixture ratio of the solvents from an initial mixture ratio to a final mixture ratio when performing a sample analysis; and b) a preparatory liquid supply controller for controlling the liquid chromatograph so as to perform, before the sample analysis, a preparatory liquid supply in which the mixture ratio of the solvents is continuously changed from the initial mixture ratio to the final mixture ratio at a rate higher than that in a case of analyzing the sample.

The "sample analysis" corresponds to the proper analysis, and the "preparatory liquid supply" to the null analysis.

The control apparatus for a liquid chromatograph according to the first aspect of the present invention may further include:

c) an analysis result storing unit for storing each analysis result of a plurality of gradient analyses in one data file; and d) an automatic data file naming unit for assigning a file name which includes at least a column name, the names of the solvents, the initial mixture ratio, or the final mixture ratio used in each of the gradient analyses to a data file containing a result of the analysis.

To solve the aforementioned problems, the second aspect of the present invention provides a control apparatus for controlling an operation of a liquid chromatograph that has a gradient analysis function in which a chromatograph analysis is performed while a mixture ratio of a plurality of solvents composing a mobile phase is temporally changed, the control apparatus including:

a) an analysis controller for controlling the liquid chromatograph so as to change the mixture ratio of the solvents from a first mixture ratio, in which an elution capability of the mobile phase is lowest in the analysis, to a second mixture ratio, in which the elution capability of the mobile phase is highest in the analysis, and then again to the first mixture ratio when performing a sample analysis; and b) a preparatory liquid supply controller for controlling the liquid chromatograph so as to perform, before the sample analysis, a preparatory liquid supply in which the mixture ratio of the solvents is changed from the first mixture ratio, which is the same as in the analysis of the sample, to the second mixture ratio, which is the same as in the analysis of the sample, and then again to the first mixture ratio, wherein:

if a plurality of sample analyses are performed and if the kind of column, kinds of solvents, the first mixture ratio, and the second mixture ratio used in two successively performed sample analyses are the same, the preparatory liquid supply controller omits the preparatory liquid supply between the two sample analyses.

The "sample analysis" here corresponds to the proper analysis, and the "preparatory liquid supply" to the null analysis. Generally speaking, the elution capability of a mobile phase in one gradient analysis is lowest at the initiation of the gradient process and highest in the washing process. Therefore, the mixture ratio of the solvents at the initiation of the gradient process is typically the first mixture ratio of the present invention, and the ratio in the washing process is the second mixture ratio of the present invention. If the elution capability of the mobile phase is sufficiently high at the termination of the gradient process, the washing process may be omitted in some cases. In this case, the mixture ratio of the solvents at that point is the second mixture ratio of the present invention.

As previously described, when two successive sample analyses have the same kind of column, kinds of solvents, the first mixture ratio, and the second mixture ratio, the sample analysis first performed plays the same role as the null analysis of the sample analysis subsequently performed. Hence, even though a null analysis is not performed before the subsequent sample analysis, a shift of the retention time as mentioned earlier will not occur. As just described, it is possible to omit a null analysis or null analyses without influencing the result of the analysis with the control apparatus for a liquid chromatograph that has the aforementioned configurations according to the second aspect of the present invention.

The control apparatus for a liquid chromatograph according to the second aspect of the present invention may further include:

c) an analysis result storing unit for storing each result of multiple gradient analyses in one data file; and d) an automatic data file naming unit for assigning a file name, which includes at least one of either a column name or names of the solvents used in each of the gradient analyses, a mixture ratio of the solvents at a point of initiation of a process of continuously changing the mixture ratio of the solvents in each of the gradient analyses, or a mixture ratio of the solvents at a point of termination of that process in each of the gradient analyses, to a data file containing a result of the analysis.

The "process of continuously changing the mixture ratio of solvents" corresponds to the gradient process.

Effects of the Invention

The control apparatus for a liquid chromatograph that has the aforementioned configurations according to the first aspect of the present invention can decrease the time required to perform a null analysis (preparatory liquid supply). Therefore, the time required for a series of analyses can be reduced when a plurality of gradient analyses are performed, as in the case of method scouting as mentioned earlier.

The control apparatus for a liquid chromatograph that has the aforementioned configurations according to the second aspect of the present invention can omit a null analysis or null analyses (preparatory liquid supply) without influencing the result of the analysis. Therefore, the time required for a series of analyses can be reduced without decreasing the accuracy of the analysis when a plurality of gradient analyses are continuously performed, as in the case of method scouting mentioned earlier.

In addition, when the control apparatus for a liquid chromatograph according to the first or second aspect of the present invention includes the automatic data file name giving unit, a user can easily ascertain the conditions of the analysis just by looking at the name of the analysis result data file without having to open the file.

BRIEF DESCRIPTION OF THE DRAWINGS

FIG. 3A shows an example of a schedule table for method scouting in a conventional apparatus, and FIG. 3B shows a schedule table for method scouting in the apparatus of the first embodiment.

FIG. 12A shows an example of a schedule table for method scouting in a conventional apparatus, and FIG. 12B shows a schedule table for method scouting in the apparatus of the second embodiment.

BEST MODES FOR CARRYING OUT THE INVENTION

The best modes for implementing the control apparatus for a liquid chromatograph according to the present invention will now be described with embodiments.

First Embodiment

Figure 1:
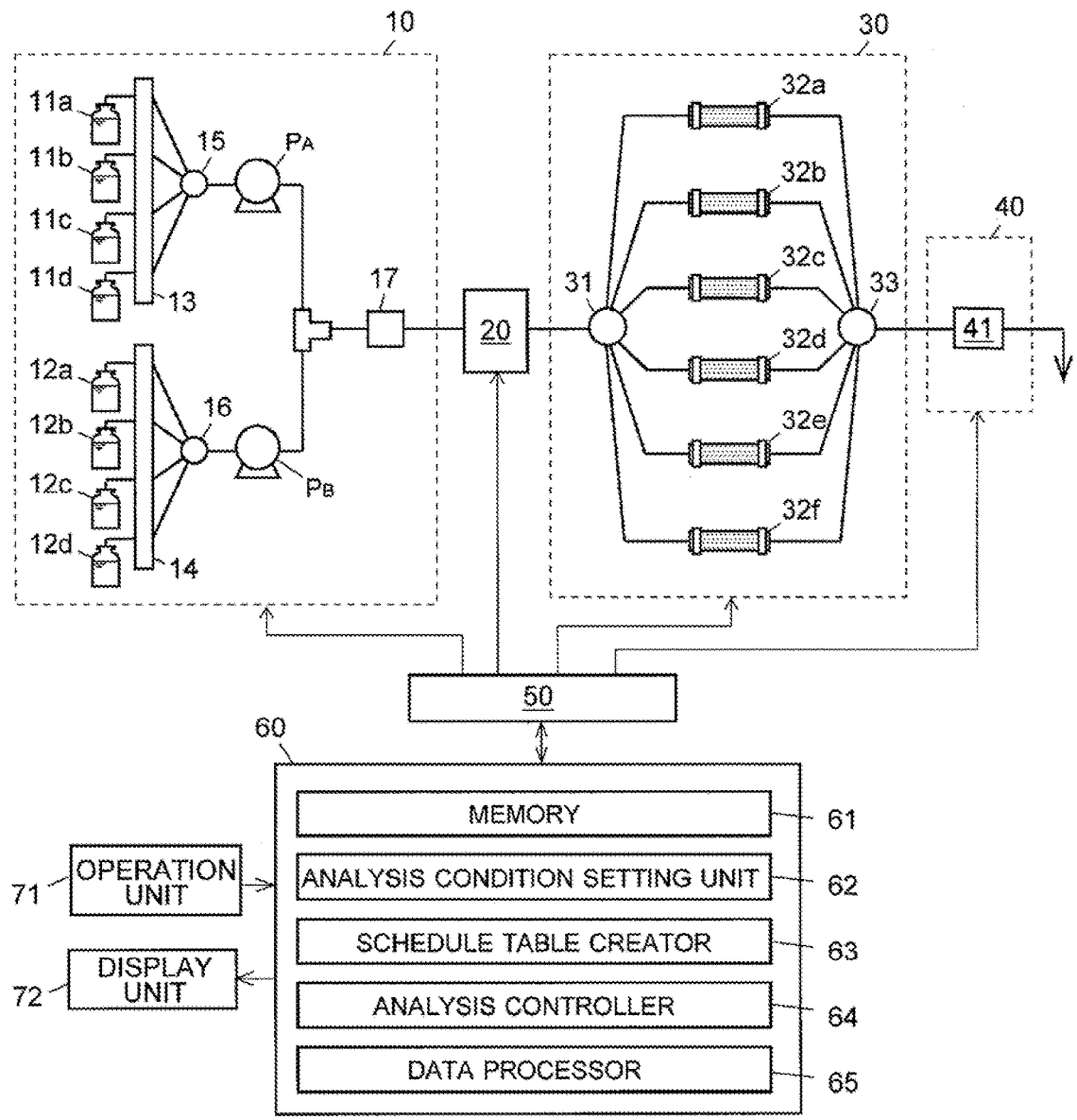
FIG. 1 is a schematic configuration diagram of a liquid chromatograph that has the control apparatus according to the first embodiment of the present invention.

The control apparatus for a liquid chromatograph according to the first embodiment of the present invention will be described with reference to FIGS. 1 through 6. FIG. 1 is a schematic configuration diagram of a liquid chromatograph that has the control apparatus according to the present embodiment.

This liquid chromatograph includes: a liquid supplier 10; an auto sampler 20; a column oven 30; a detection unit 40; a system controller 50 for controlling each of these units; a controller 60 for managing analysis operations through the system controller 50 and for analyzing and processing the data obtained by the detector 40; an operation unit 71 composed of a keyboard and a mouse connected to the controller 60; a display unit composed of a display; and other units.

The liquid supplier 10 mixes the solvent A which has been drawn by the pump $P_A$ and the solvent B which has been drawn by the pump $P_B$ and then supplies the mixed solvent to the column. Four solvent containers are connected to each of the pumps $P_A$ and $P_B$ through solvent selector valves 15 and 16 as well as through deaerator units 13 and 14, respectively. An aqueous solvent (i.e. a solvent composed mainly of water), for example, is contained in the solvent containers 11a through 11d which are connected to the pump $P_A$. By operating the solvent selector valve 15, one of the four solvent containers 11a through 11d is selected and the solvent in the selected container is drawn as the solvent A by the pump $P_A$. An organic solvent (i.e. a solvent composed mainly of an organic solvent), for example, is contained in the solvent containers 12a through 12d which are connected to the pump $P_B$. By operating the solvent selector valve 16, one of the four solvent containers 12a through 12d is selected and the solvent in the selected container is drawn as the solvent B by the pump $P_B$. The flow rate of each of the pumps $P_A$ and $P_B$ can be controlled so as to change as time progresses, which allows the solvent to be supplied in a gradient method in which the mixture ratio of the solvents A and B temporally changes. The column oven 30 includes six columns 32a through 32f, and passage selection units 31 and 33 for selectively connecting any one of these columns to the passage of the mobile phase. A detector 41, such as a PDA detector, is provided in the detection unit 40.

The controller 60 includes a memory 61, an analysis condition setting unit 62, a schedule table creator 63, an analysis controller 64, and a data processor 65 as function blocks. The controller 60 is actually a personal computer, and a variety of functions which will be described later are achieved by executing dedicated control/process software installed in the personal computer. The analysis controller 64 corresponds to the analysis controller and the preparatory liquid supply controller of the first aspect of the present invention, and the data processor 65 corresponds to the analysis result storing unit and the automatic data file naming unit of the second aspect of the present invention.

A general analytical operation in a single gradient analysis using the aforementioned liquid chromatograph is as follows. Under the control of the system controller 50 which receives directions from the analysis controller 64 of the controller 60, each of the solvent selector valves 15 and 16 selects one solvent container, and the pumps $P_A$ and $P_B$ draw the solvent from the solvent containers at a predetermined flow rate. The solvent A drawn by the pump $P_A$ and the solvent B drawn by the pump $P_B$ are homogeneously mixed by the gradient mixer 17, and the mobile phase after the mixture process flows into the column through the auto sampler 20. A rack in which one or more sample bottles (vials) are mounted is set in the auto sampler 20. A sample is selected and collected under the control of the system controller 50, and the sample is injected into the mobile phase at a predetermined time. This sample is introduced with the mobile phase into one of the columns 32a through 32f.

Figure 6:
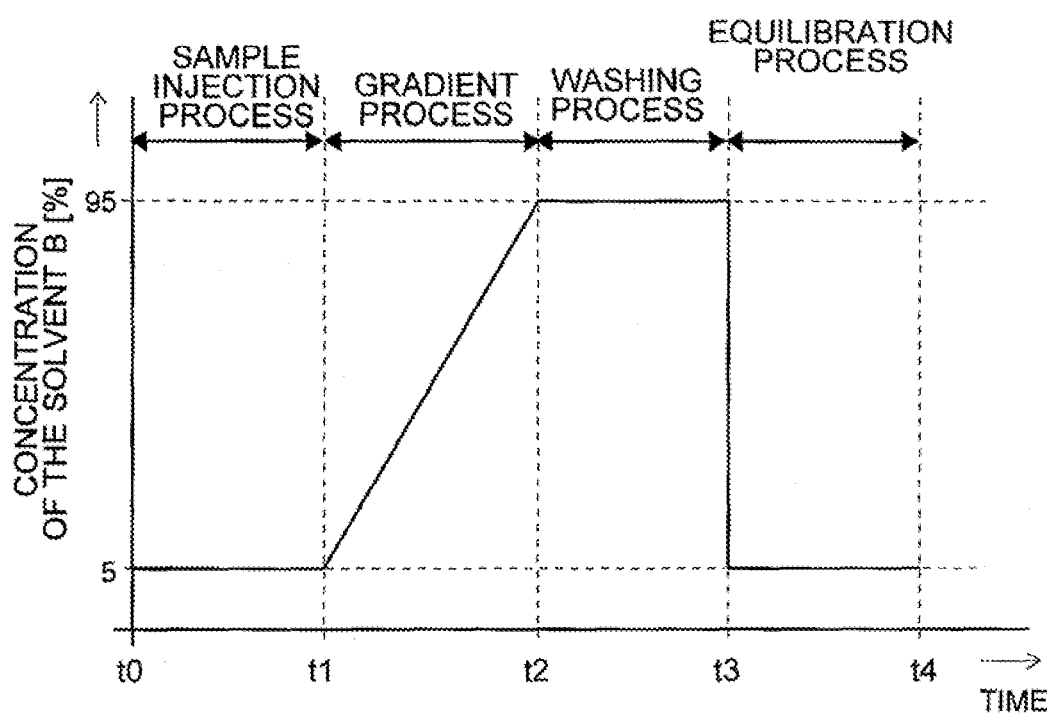
FIG. 6 shows an example of a gradient profile.

At this stage, from the point in time when the sample is injected until a predetermined period of time has elapsed, the flow rates of the pumps $P_A$ and $P_B$ are controlled so that the ratio of the solvent B is low and that of the solvent A is high, as shown in the gradient profile of FIG. 6 (time t0 through t1: sample introduction process). Since a solvent having a low elution capability is used as the solvent A, the components in the sample are temporarily adsorbed in the column. Subsequently, the flow rates of the pumps $P_A$ and $P_B$ are changed as time progresses so as to increase the ratio of the solvent B (time t1 through t2: gradient process). Since a solvent having a high elution capability is used as the solvent B, the components adsorbed in the column are sequentially eluted from the column in accordance with their polarity and introduced into the detection unit 40.

After that, each component is sequentially detected by the detector 41 provided in the detection unit 40, and the data obtained by digitizing the detection signal that corresponds to the component concentration are sent to the controller 60 through the system controller 50. In the controller 60, the received data are stored in the memory 61 which is provided in a memory unit such as a hard disk, and a predetermined process is performed on the data by the data processor 65 to create a chromatogram and to display it on the screen of the display unit 72. Subsequently, the solvent B is supplied at a high concentration for a given period of time to wash the column (time t2 through t3: washing process), and then the composition of the mobile phase is returned to the initial state to equilibrate the column for a given period of time (time t3 through t4: equilibration process).

Figure 2:
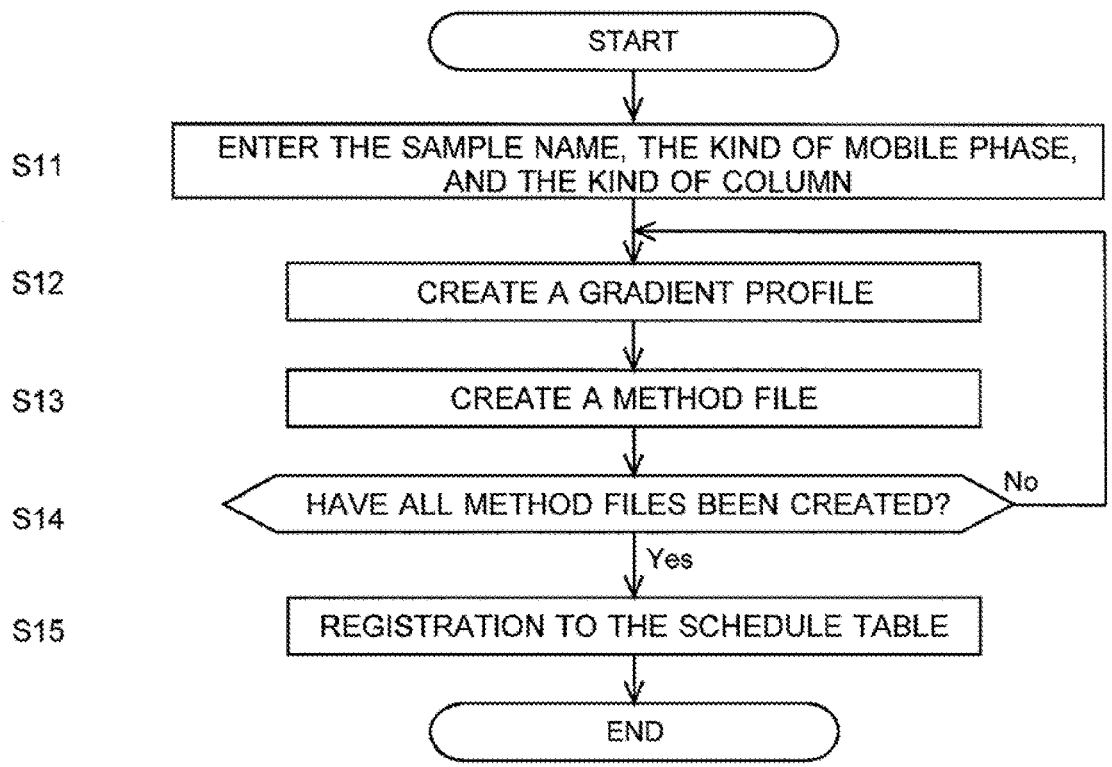
FIG. 2 is a flowchart showing the operation of the control apparatus according to the first and second embodiments of the present invention.

Next, the operation when creating a method file and a schedule table will be described with reference to the flowchart of FIG. 2 in order to explain the specific operation in the control apparatus for a liquid chromatograph of the present embodiment.

First, a user operates the operation unit 71 to order the analysis condition setting unit 62 to perform method scouting by means of a gradient analysis. Then, a settings screen (not shown) is shown on the display of the display unit 72. The user selects the name of the sample to be analyzed, the injection amount of the sample, the kind of the solvent which is used as the solvent A, the kind of the solvent which is used as the solvent B, the kind of the column, and other information on the settings screen (Step S11).

After finishing the setup on the settings screen, a gradient condition entry screen (not shown) is shown on the display of the display unit 72. Then the user sets the gradient conditions to be applied in one gradient analysis. The "gradient conditions" include the execution times of the sample introduction process, the gradient process, the washing process, and the equilibration process, the composition of the mobile phase at the point of both initiation and termination of the gradient process, and the composition in the washing process. After the user has entered these values, the analysis condition setting unit 62 creates a gradient profile as shown in FIG. 6 (Step S12). The composition of the mobile phase at the point in time when the gradient process is initiated corresponds to the initial mixture ratio in the first aspect of the present invention, and the composition of the mobile phase at the point in time when the gradient process is finished corresponds to the final mixture ratio in the first aspect of the present invention. The composition of the mobile phase may be specified by the ratio of the solvent B in the mixed liquid of the mobile phase (i.e. solvent A+solvent B), for example.

When the user then enters an instruction to create a method file through the operation unit 71, a single method file is created based on the information set in the previous steps and is stored in the memory 61 (Step S13). This method file contains parameters such as the kinds of the solvents A and B and the kind of the column which have been entered in Step S11 and the gradient profile created in Step S12.

Subsequently, repeatedly performing Steps S12 and S13 creates a gradient profile and a method file for each of any number of gradient analyses to be performed in method scouting. As a consequence, a plurality of method files are created in which only the gradient profiles are different, while the other parameters remain the same.

In this embodiment, the user enters the gradient profile for each analysis and sets them one by one. However, the setting of the gradient profile is not limited to this method only. For example, the user may be asked to specify the following information: the fundamental gradient conditions; the number of mobile phase compositional changes at the initiation and termination points of the gradient process; and how the mobile phase composition is changed at every step of the change. The analysis condition setting unit 62 may then create, from the fundamental gradient conditions, multiple kinds of gradient profiles in which the mobile phase compositions at the initiation and termination points of the gradient process are changed in stages, and create method files that include each of the gradient profiles to be stored in the memory 61.

After the method files for all the gradient profiles to be performed are created (i.e. "Yes" at Step S14), the user subsequently performs a predetermined operation using the operation unit 71 to instruct the schedule table creator 63 to create a schedule table. As a consequence, a schedule table as shown in FIG. 3B is created and displayed on the screen of the display unit 72. In this table, each row corresponds to a gradient analysis, and a single row contains the information required to perform the analysis, such as the sample name, sample injection amount, method file name, data file name, and other information.

In a conventional apparatus, analyses using the same method file are listed in two consecutive rows, as shown in FIG. 3A, in which the first row corresponds to a null analysis and the second row to a proper analysis. Since there is no need to introduce a sample in a null analysis, the row corresponding to a null analysis contains neither the sample name nor the sample injection amount. Likewise, in the apparatus of the present embodiment, a row for a null analysis in which a sample is not introduced is listed prior to a row for a proper analysis as shown in FIG. 3B. However, the method file name described in a row for a null analysis is different from that in a proper analysis. The method file (e.g. "method file 1") specified in the row for a null analysis is created based on the method file (e.g. "method file 1") specified in the row for the proper analysis corresponding to that null analysis. The information contained in these two method files is identical, apart from the execution time of the gradient process in the gradient profile.

Figure 4A:
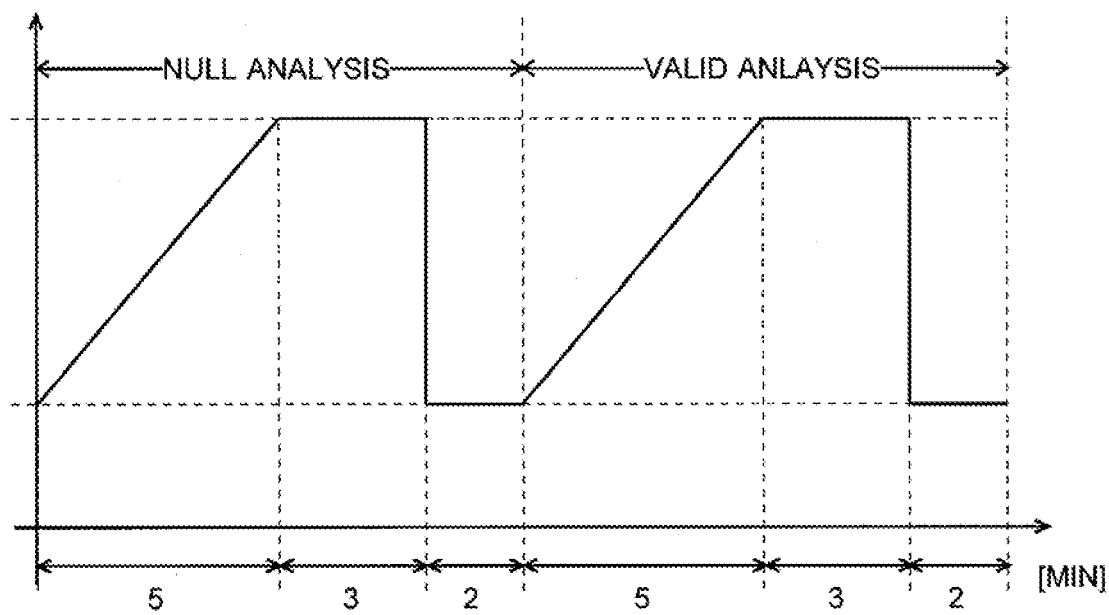
FIG. 4A shows a time chart of the compositional change of the mobile phase when a null analysis and a proper analysis are performed in a conventional apparatus.
Figure 4B:
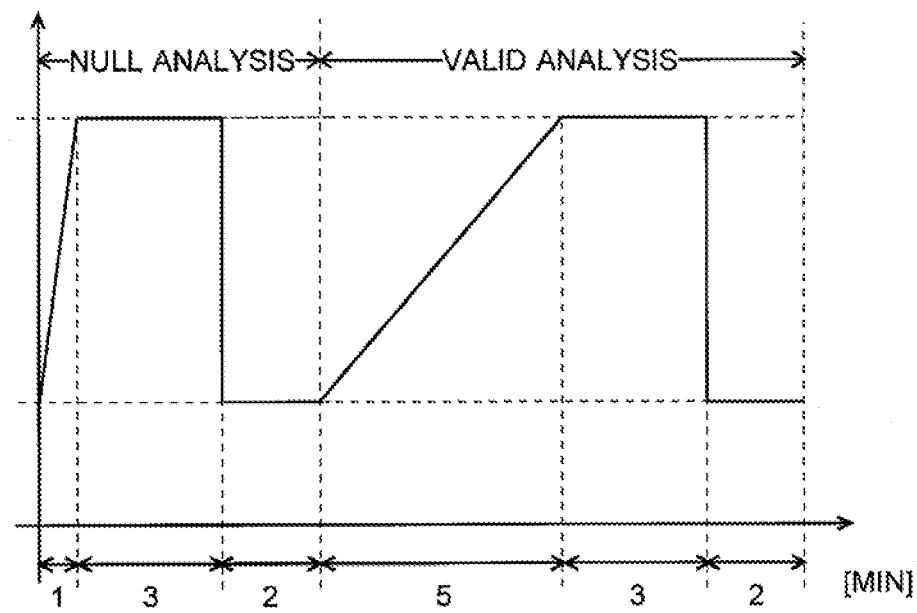
FIG. 4B shows a time chart from the apparatus of the first embodiment.

FIG. 4B shows an example of a time chart of the changing mobile phase composition in the sequential performance of a null analysis and a proper analysis. This corresponds to the gradient profile described in the method file 1' (left side) and that described in the method file 1 (right side). In this example, the sample introduction process is omitted. As shown in FIG. 4B, when comparing the gradient profile of the null analysis and that of the proper analysis, the execution times of the washing process and the equilibration process are the same, and the mobile phase compositions at the initiation and termination of the gradient process are the same, whereas the execution time of the gradient process in the null analysis is shorter than that in the proper analysis. (Therefore, the gradient of the change of the mobile phase composition is steep in the null analysis.) In particular, although the washing process and the equilibration process are respectively performed for three and two minutes in both the proper analysis and the null analysis, the gradient process is performed for five minutes in the proper analysis and for one minute in the null analysis. Therefore, in this example, it is possible to reduce the time required from the initiation of the null analysis until the termination of the proper analysis by four minutes in comparison to the case where the same gradient profile is applied to both the null analysis and the proper analysis, as shown in FIG. 4A.

Figure 5:
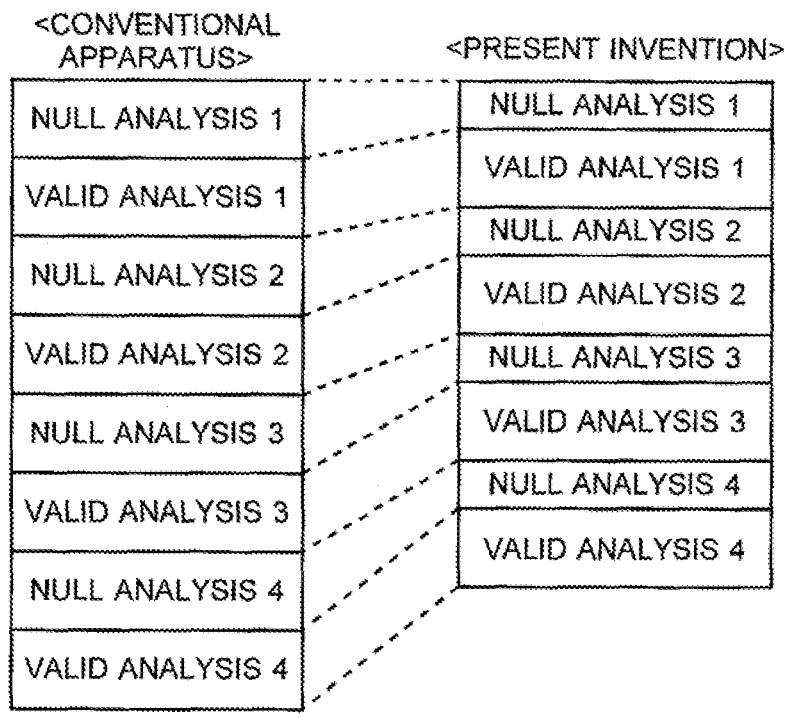
FIG. 5 is a schematic diagram for explaining the effect of the apparatus of the first embodiment.

In addition, since plural pairs of such null analyses and proper analyses are sequentially performed in method scouting, as shown in FIG. 5, decreasing the time required for each null analysis as previously described leads to a great reduction of the time required for the entire analysis.

The method files (method 1', method 2', etc.) for a null analysis are automatically created by the analysis condition setting unit 62 when the instruction to create a schedule table is entered and stored in the memory 61. The creation of each of the method files for the null analysis is based on the method files created in Step S13. In this process, the amount by which the execution time of the gradient process in the null analysis is reduced in comparison to that of the proper analysis (e.g. three minutes less than in a proper analysis, 20% of the proper analysis, etc.) is determined in advance by the user and memorized in the memory 61.

As previously described, the data file name used for storing the result of the analysis is described in each row of the schedule table. In conventional apparatuses, a serial number or other characters are used as the data file name, whereas a file name showing the analysis conditions as illustrated in FIG. 3B is automatically used in the apparatus of the present embodiment. In the example of FIG. 3B, the data file name is as follows: (prefix)_(column name)_(name of the solvent A)_(name of the solvent B)_(composition ratio of the solvent B when the gradient process is initiated)_(composition ratio of the solvent B when the gradient process is finished). The prefix is a string of letters set by the user in advance and it is common to all rows. Appropriate strings of letters are entered for the portions other than the prefix according to the description of the method file in the same row.

After that, when the user performs a predetermined operation to execute the initiation of the analysis, an automatic analysis begins in accordance with the schedule table, and gradient analyses with a variety of gradient profiles are sequentially performed.

The chromatogram data obtained as a result of each analysis are stored in a single data file for every analysis. For each file, a data file name is assigned which is described in the corresponding row in the schedule table. Consequently, the user can easily ascertain the conditions of the analysis just by looking at the name of the analysis result data file without having to open it.

In the aforementioned example of FIG. 3B, the same data file name is used in both the proper analysis row and in the corresponding null analysis row. Hence, the data file created by executing the null analysis will be overwritten by the data file of the proper analysis which will be performed immediately after the null analysis. This will not cause any problems as it is unlikely that the user will refer to the result of the null analysis. Alternatively, the result of the null analysis and that of the proper analysis may be stored with different data file names. For example, a character or characters for distinguishing a null analysis from a proper analysis may be added at the end of the file name. A conventional serial number or other characters may also be added to the null analysis data file name so that the user can easily distinguish the data file of a null analysis from that of a proper analysis. As an alternative, the data file of a null analysis and that of a proper analysis may be saved in different locations.

Second Embodiment

The control apparatus for a liquid chromatograph according to the second embodiment of the present invention will be described with reference to FIGS. 2 and 7 through 14.

The control apparatus of this embodiment has the same configurations as the liquid chromatograph that has this control apparatus, as shown in FIG. 1, which was described earlier. Hence, the configuration explanations are omitted. In this embodiment, the schedule table creator 63 and the analysis controller 64 work together and serve as the analysis controller and the preparatory liquid supply controller in the aforementioned second aspect of the present invention. The data processor 65 corresponds to the analysis result storing unit and the automatic data file naming unit in the aforementioned second aspect of the present invention.

Figure 14:
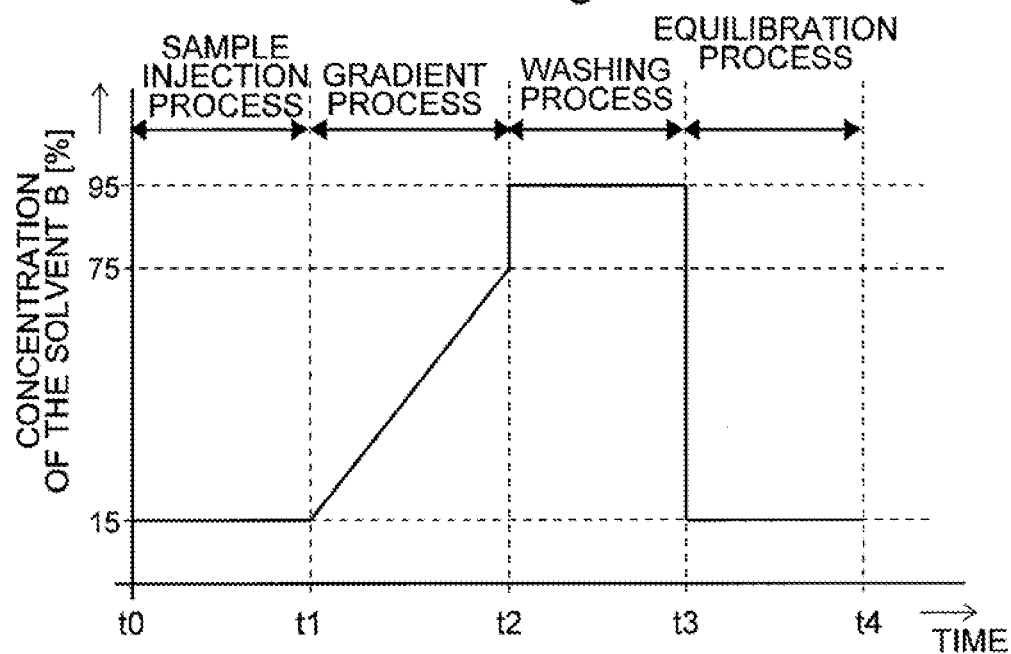
FIG. 14 shows an example of a gradient profile.
Figures 15, 16:
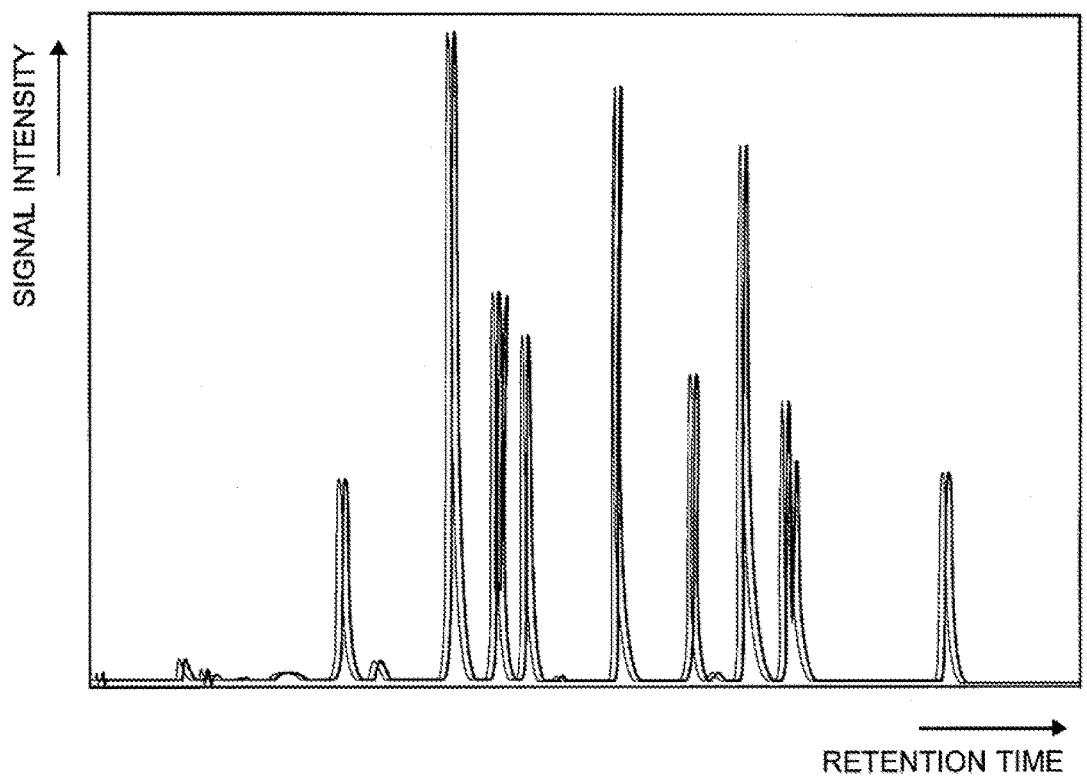
FIG. 15 shows a conventional schedule table.
FIG. 16 is a chromatogram showing the result after a gradient analysis was performed three times consecutively for the same sample under the same conditions.

The standard analysis operation in a single gradient analysis using the liquid chromatograph of the present embodiment (i.e. the operations in the sample introduction process, the gradient process, the washing process, and the equilibration process) has also been omitted as it is the same as that in the aforementioned embodiment. In the present embodiment, as shown in FIG. 14 (and FIGS. 8 through 11), the concentration of the solvent B during the washing process is set higher than at the gradient process completion point. However, the concentration levels may also be set at the same level, as shown in FIG. 6.

Next, the operation for creating a method file and a schedule table in the control apparatus for a liquid chromatograph of the present embodiment will be described with reference to the flowchart of FIG. 2.

First, the user operates the operation unit 71 to enter and set the sample name, the kind of mobile phase, the kind of column, and other information (Step S11), and then enters and sets the gradient conditions. The analysis condition setting unit 62 next creates a gradient_profile as shown in FIG. 14 (Step S12). In the liquid chromatograph of the present embodiment, columns 32*a* through 32*f* are employed as the reverse phase chromatography column, and the polarity of the solvent B is smaller than that of the solvent A. Hence, increasing the ratio of the solvent B in the mobile phase raises the elusion elution capability of the mobile phase (i.e. the capability of eluting the sample components from the column).

The mobile phase compositions in the sample introduction process and in the equilibration process are identical to that of the initiation point of the gradient analysis. Therefore, when the user sets the mobile phase composition for the initiation of the gradient process, the mobile phase compositions in those processes are also determined automatically. The mobile phase composition in the washing process is set so that that the elution capability is the same or higher than at the gradient process completion point. Hence, in a single gradient analysis, the elution capability of the mobile phase is lowest when the gradient process is initiated (as well as in the sample introduction process and in the equilibration process), and is highest in the washing process. Accordingly, the mobile phase composition at the initiation of the gradient process corresponds to the first mixture ratio in the second aspect of the present invention, and the mobile phase composition in the washing process corresponds to the second mixture ratio in the second aspect of the present invention.

The other aspects of Steps S11 and S12 are as described in the first embodiment, and therefore the detailed explanations are omitted.

Subsequently, when the user operates the operation unit 71 to instruct it to create a method file, a method file is created based on the information previously set and is stored in the memory 61 (Step S13). This method file contains parameters such as the kinds of the solvents A and B and the kind of column, which were entered in Step S11, as well as the gradient profile that was created in Step S12.

After that, repeatedly performing Steps S12 and S13 creates a gradient profile and a method file for each of any number of gradient analyses to be performed in method scouting. Consequently, multiple method files with different analysis conditions are created and stored in the memory 61. Hereinafter, the method files will be called method 1, method 2, and so on.

In this embodiment, the user enters the gradient profile for each analysis and sets them one by one. However, the setting of the gradient profile is not limited to this method only. For example, the user may be asked to specify the following information: the fundamental gradient conditions; the number of mobile phase compositional changes at the initiation and termination points of the gradient process; and how the mobile phase composition is changed at every step of the change. The analysis condition setting unit 62 may then create, from the fundamental gradient conditions, multiple kinds of gradient profiles in which the mobile phase compositions at the initiation and termination points of the gradient process are changed in stages, and create method files that include each of the gradient profiles to be stored in the memory 61.

After all the method files which will be used in the method scouting have been created (i.e. "Yes" at Step S14), the user subsequently performs a predetermined operation using the operation unit 71 to instruct the schedule table creator 63 to create a schedule table. As a consequence, a null analysis and a proper analysis using each method file are registered in a schedule table (Step S15).

Figure 7:
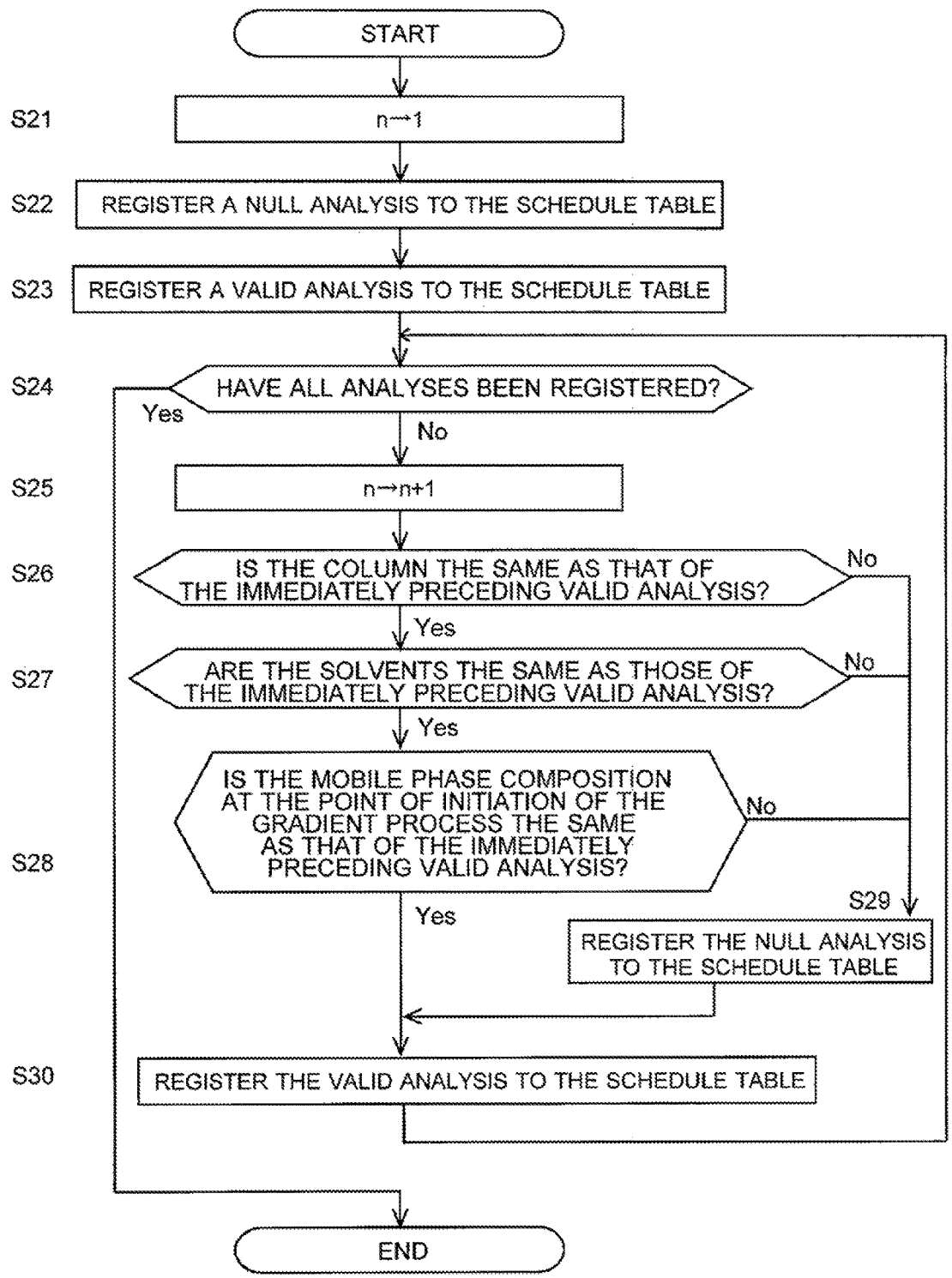
FIG. 7 is a flowchart showing the operation of the schedule table creator in the second embodiment of the present invention.

Hereinafter, the operation of the schedule table creator 63 at this point in time will be described with reference to the flowchart of FIG. 7. First, the schedule table creator 63 sets the variable n, which represents the method file number, to be 1 (Step S21), and registers the null analysis which uses the first method file (i.e. method 1) in the first row of the schedule table among the multiple method files created in Step S13 (Step S22). As previously described, samples are not introduced in a null analysis. Hence, the sample name and the sample injection amount are not described in the first row of the schedule table. The schedule table creator 63 then registers the proper analysis which uses the first method file in the second row of the schedule table (Step S23). In this process, the data set by the user in Step S11 are recorded in the sample name and the sample injection amount fields.

After that, the schedule table creator 63 determines whether or not all the method files created in Step S13 have been registered in the schedule table (Step S24). If it is determined to be "No" in Step S24, the variable n is incremented (Step S25).

Next, the schedule table creator 63 compares the content described in the second method file (i.e. method 2) with the contents of the method file used in the immediately preceding proper analysis (i.e. method 1) to determine whether or not both method files have the same kind of column (Step S26), the same kinds of solvents A and B (Step S27), and that the mobile phase composition at the initiation point of the gradient process in the gradient profile is the same (Step S28). If all of them are the same (i.e. "Yes" at all Steps S26 through 28), the proper analysis which uses the aforementioned second method file is registered in the third row of the schedule table (Step S30), and then the process returns to Step S24 (that is, the null analysis which uses the method 2 is not registered in the schedule table).

On the other hand, if it was determined to be "No" at any one of Steps S26 through S28, the null analysis which uses the second method file is registered in the third row of the schedule table (Step S29), and the proper analysis which uses the same method file is registered in the fourth row of the schedule table (Step S30). After that, the process returns to Step S24. In this process, neither the sample name nor the sample injection amount are described in the row of the null analysis, whereas both the sample name and the injection amount, as set by the user in Step S11, are described in the row of the proper analysis.

After that, the processes of Steps S24 through S30 are repeatedly performed until "Yes" is given in Step S24 (i.e. until all the method files are registered in the schedule table).

In the aforementioned examples, whether or not the mobile phase composition in the washing process is the same in both method files is not determined. This is because the same mobile phase composition in the washing process is usually set for all method files. However, if it is possible that the mobile phase compositions in the washing process vary between the method files, it is preferable to determine whether or not the columns, the solvents, and the mobile phase compositions at the initiation of the gradient process are the same (Steps S26 through S28) and further whether or not the mobile phase composition in the washing process is the same. If the answer to any one of these is "No," both the null analysis and the proper analysis are registered for that method file (Steps S29 and S30). If all of them are "Yes," the registration of the null analysis is omitted and the proper analysis is registered (Step S30).

As previously described, in the controller 60 according to the present embodiment, it is determined whether the kind of column, the kinds of the solvents, and the mobile phase composition at the initiation of the gradient process are identical in both consecutively performed proper analyses. If all the determinations are "Yes," the null analyses will be omitted between both analyses. This operation will now be described using a concrete example.

For example, consider the case where the gradient profile shown as a solid line in FIG. 8 (profile 1) is described in the method 1, and the gradient profile shown as a dashed line in FIG. 8 (which will hereinafter be called the "profile 2") is described in the method 2. The kind of column and the kinds of solvents are assumed to be the same in both methods 1 and 2.

Figure 8:
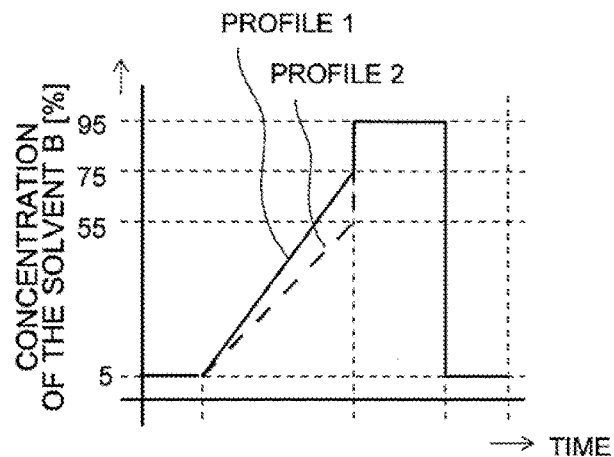
FIG. 8 shows an example of a gradient profile of the second embodiment.

As shown in FIG. 8, only the mobile phase composition at the completion point of the gradient process is different between the profile 1 and the profile 2, whereas the other conditions are the same. That is, the execution times of the sample introduction process, the gradient process, the washing process, and the equilibration process, as well as the mobile phase composition at the initiation point of the gradient process, and the mobile phase composition in the washing process are the same.

Figure 9A:
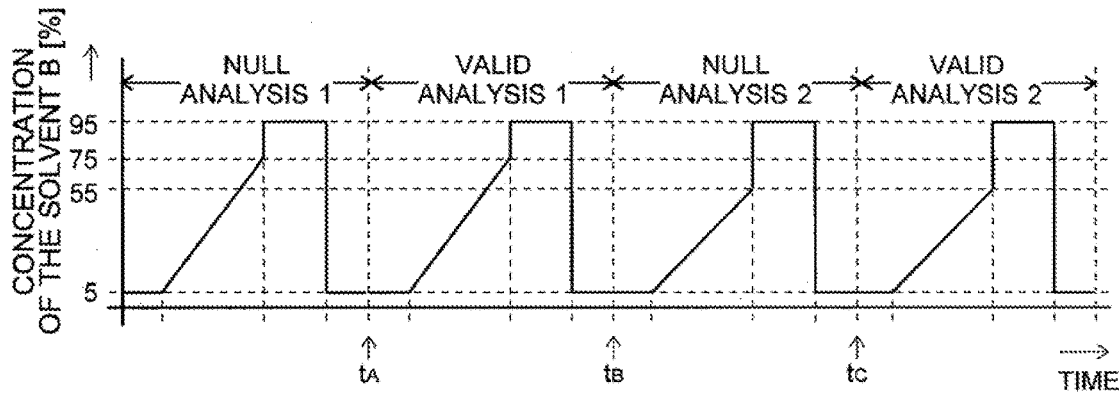
FIG. 9A is a time chart showing an example of mobile phase composition change when a null analysis and a proper analysis are performed in a conventional apparatus.

In a conventional apparatus, in order to register the method 1 in which the profile 1 is described and the method 2 in which the profile 2 is described in a schedule table, a null analysis using the method 1 (null analysis 1), a proper analysis using the method 1 (proper analysis 1), a null analysis using the method 2 (null analysis 2), and the proper analysis using the method 2 (proper analysis 2) are registered in that order. FIG. 9A shows the time chart that demonstrates the mobile phase composition change in this case. This is equivalent to four profiles in which two "profile 1" and two "profile 2" (as shown in FIG. 8) are aligned.

As previously described, in both the profile 1 and the profile 2, the mobile phase composition at the point of initiation of the gradient process is the same (concentration of the solvent B: 5%), and the mobile phase composition in the washing process is also the same (concentration of the solvent B: 95%). Therefore, in the time chart as shown in FIG. 9A, the process of changing the mixture ratio of solvent B from 5% to 95% and then back to 5% is repeated four times. In this case, the equilibrated states of the column are probably the same at the initiation times $t_A$, $t_B$, and $t_C$ of the second process, the third process, and the fourth process, i.e. the proper analysis 1, the null analysis 2, and the proper analysis 2, respectively. This indicates that even if the sample is introduced at the initiation time $t_B$ of the null analysis 2 of FIG. 9A, the result of the analysis will probably be identical to that which is obtained when the sample is introduced at the initiation time $t_C$ of the proper analysis 2.

Figure 9B:
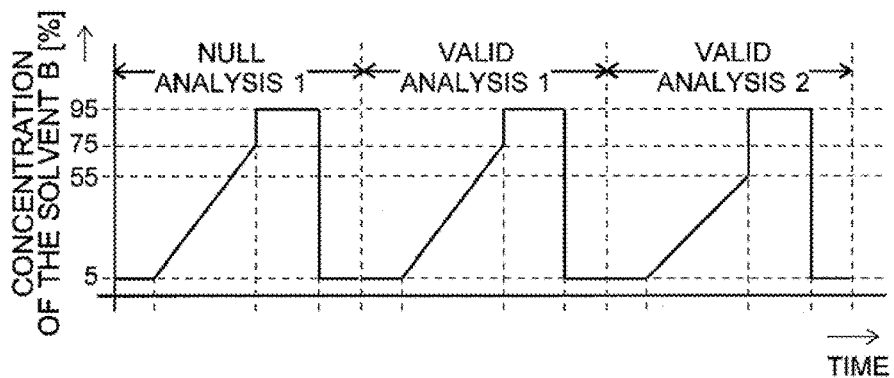
FIG. 9B shows that of the apparatus of the second embodiment.

Due to this factor, in the controller 60 of the present embodiment, the null analysis 2 is omitted, and the null analysis 1, the proper analysis 1, and the proper analysis 2 are registered in the schedule table in that order. FIG. 9B shows the time chart of the change of the mobile phase composition in this embodiment. This is equivalent to the alignment of two "profile 1" and one "profile 2" (profiles as shown in FIG. 8). Consequently, the time required from the initiation of the null analysis 1 until the termination of the proper analysis 2 can be reduced more than ever before.

Figure 10:
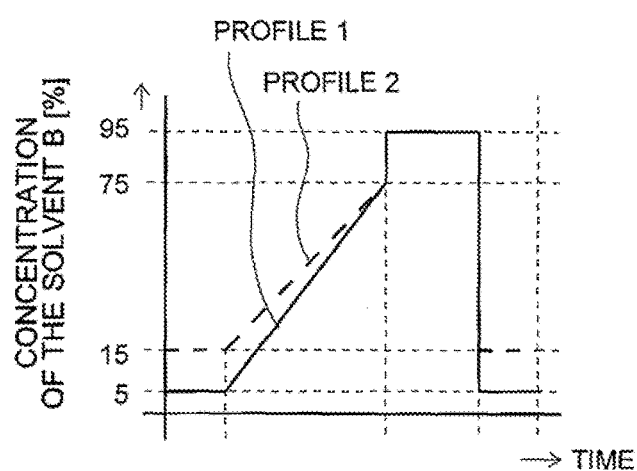
FIG. 10 shows another example of the gradient profile in the second embodiment.
Figure 11:
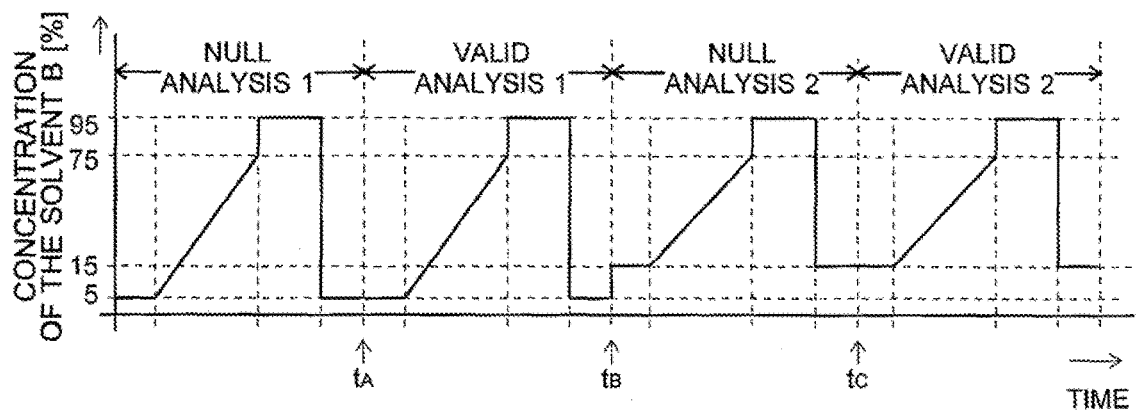
FIG. 11 is a time chart showing another example of the compositional change of the mobile phase when a null analysis and a proper analysis are performed.

On the other hand, as shown in FIG. 10, for example, if the mobile phase composition at the initiation of the gradient process differs between the profile 1 and the profile 2, the null analysis 1, the proper analysis 1, the null analysis 2, and the proper analysis 2 are registered in the schedule table in that order, which is conventionally done and is also done in the apparatus of the present embodiment. FIG. 11 shows the time chart of the mobile phase composition change in this case. This is equivalent to the alignment of two "profile 1" and two "profile 2" (profiles as shown in FIG. 10).

As previously described, the mobile phase composition at the initiation of the gradient process differs between the profile 1 and the profile 2 in FIG. 10. This means that it is probable that the equilibrated state of the column differs at each of initiation times $t_A$, $t_B$, and $t_C$ of the proper analysis 1, the null analysis 2, and the proper analysis 2, respectively, in the time chart of FIG. 11. Therefore, the null analysis 2 cannot be omitted in this case.

FIG. 12B shows an example of the schedule table created by the control apparatus for a liquid chromatograph of the present embodiment. In this table, each row corresponds to an analysis. A row contains the information required to perform the analysis, such as the sample name, sample injection amount, method file name, data file name, and other information. In the rows for a null analysis, the sample name and sample injection amount are not described, since there is no need to introduce a sample in a null analysis.

Figure 13:
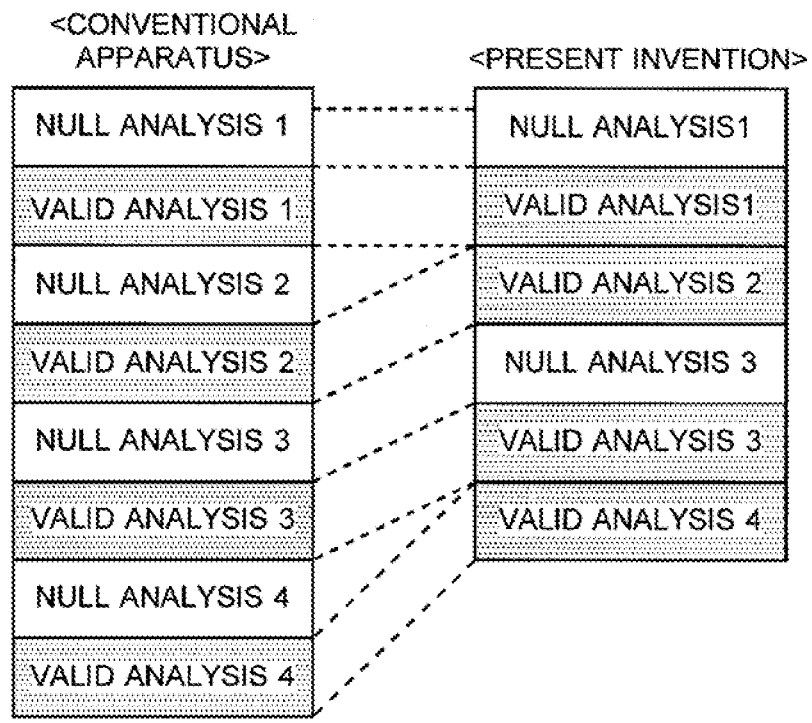
FIG. 13 is a schematic diagram for explaining the effect of the apparatus of the second embodiment.

In the example of this schedule table, the mobile phase composition at the initiation of the gradient process is different in methods 2 and 3, but it is the same in methods 1 and 2 as well as methods 3 and 4. Even in such cases, a proper analysis and a null analysis are registered for all the method files as shown in FIG. 12A in a conventional apparatus. In the apparatus of the present embodiment, however, the null analyses between the proper analyses 1 and 2 and between the proper analyses 3 and 4 (i.e. null analyses 2 and 4) are omitted as shown in FIG. 13. Accordingly, in the schedule table of FIG. 12B, the analyses using the methods 1 and 3 are each registered in two rows, whereas the analyses using the methods 2 and 4 are each registered in only one row.

As just described, it is possible to omit a null analysis or null analyses without influencing the result of the analysis in the present embodiment. This enables the time required for a series of analyses to be reduced without decreasing the accuracy of the analysis in method scouting or other types of analysis.

As previously described, the name of the data file in which the result of the analysis is stored is noted in each row of the schedule table. File names indicating the analysis conditions, as shown in FIG. 12B, may preferably be used automatically in this embodiment. In the example of FIG. 12B, the data file name is as follows: (prefix)_(column name)_(name of the solvent A)_(name of the solvent B)_(composition ratio of the solvent B when the gradient process is initiated)_(composition ratio of the solvent B when the gradient process is finished). The prefix used in the file name is common to all rows and is a string of letters set by the user in advance. Appropriate strings of letters are entered for anything other than the prefix based on the description of the method file in the same row.

After that, when the user performs a predetermined operation to execute the initiation of the analysis, an automatic analysis begins in accordance with the schedule table, and gradient analyses with a variety of gradient profiles are sequentially performed.

The chromatogram data obtained as a result of each analysis are stored in a single data file for every analysis. For each file, a data file name is assigned which is described in the corresponding row in the schedule table. Consequently, the user can easily ascertain the conditions of the analysis just by looking at the name of the analysis result data file without having to open it.

In the aforementioned example of FIG. 12B, the same data file name is used in both the proper analysis row and in the corresponding null analysis row. Hence, the data file created by executing the null analysis will be overwritten by the data file of the proper analysis which will be performed immediately after the null analysis. This will not cause any problems as it is unlikely that the user will refer to the result of the null analysis. Alternatively, the result of the null analysis and that of the proper analysis may be stored with different data file names. For example, a character or characters for distinguishing a null analysis from a proper analysis may be added at the end of the file name. A conventional serial number or other characters may also be added to the null analysis data file name so that the user can easily distinguish the data file of a null analysis from that of a proper analysis. As an alternative, the data file of a null analysis and that of a proper analysis may be saved in different locations.

Implementation modes for the present invention have until now been described by using the embodiments. It should be noted that the present invention is not limited to the aforementioned embodiments, and appropriate changes made within the spirit of the present invention are allowed. For example, in the aforementioned example, it is determined whether or not the kind of column, the kind of the solvents, and the mobile phase composition at the initiation of the gradient process are the same in two successive proper analyses. If all of them are the same, the null analysis between the two proper analyses is omitted. In addition to this, it is possible to determine whether or not any one of the execution times of the sample introduction process, the gradient process, the washing process, and the equilibration process in each proper analysis is the same in the two proper analyses. In this case, if the two proper analyses have the same kind of column, kind of solvent, and mobile phase composition at the initiation of the gradient process, and if any of the execution times are the same in both of the proper analyses, the null analysis between the two proper analyses is omitted. However, if any one of them is not the same, the null analysis is not omitted.

In the aforementioned embodiments, the method files for two successive analyses are compared one by one and sequentially registered in the schedule table. However, it is possible to register all the method files in the schedule table and then collectively compare the adjacent method files. The comparison may then be performed after the proper analysis rows and the null analysis rows for all the method files have first been registered in the schedule table. By so doing, only the row or rows of the null analysis or analyses determined to be omissible may be deleted. Alternatively, the comparison may be performed after only the proper analyses rows for all the method files have first been registered in the schedule table. Then, a null analysis row using the method file may be inserted for the method file or files of the null analysis or analyses which have been determined not to be omissible. In addition, the existence of identical analyses in the table may be determined after all the method files have been registered in the schedule table. If identical analyses are found, all except one may be deleted. This can further reduce the time required for method scouting.

EXPLANATION OF NUMERALS

10 . . . Liquid Supplier
11a through 11d and 12a through 12d . . . Solvent Container
$P_A$, $P_B$ . . . Pump
15, 16 . . . Solvent Selector Valve
17 . . . Gradient Mixer
20 . . . Auto Sampler
30 . . . Column Oven
32a through 32f . . . Column
40 . . . Detection Unit
41 . . . Detector
50 . . . System Controller
60 . . . Controller
61 . . . Memory
62 . . . Analysis Condition Setting Unit
63 . . . Schedule Table Creator
64 . . . Analysis Controller
65 . . . Data Processor
71 . . . Operation Unit
72 . . . Display Unit

The invention claimed is:

1. A control apparatus for controlling an operation of a liquid chromatograph that has a gradient analysis function in which a chromatograph analysis is performed while a mixture ratio of a plurality of solvents composing a mobile phase is temporally changed, the control apparatus comprising:
   a) an analysis controller programmed to control the liquid chromatograph so as to continuously change the mixture ratio of the solvents from an initial mixture ratio to a final mixture ratio when performing a sample analysis; and
   b) a preparatory liquid supply controller programmed to control the liquid chromatograph so as to perform, before the sample analysis, a preparatory liquid supply in which the mixture ratio of the solvents is continuously changed from the initial mixture ratio to the final mixture ratio at a rate higher than that in the sample analysis so that a time required to perform the preparatory liquid supply is reduced.

2. The control apparatus for a liquid chromatograph according to claim 1, further comprising:
   c) an analysis result storing unit programmed to store each analysis result of a plurality of gradient analyses in one data file; and
   d) an automatic data file naming unit programmed to assign a file name which includes at least a column name, names of the solvents, the initial mixture ratio, or the final mixture ratio used in each of the gradient analyses to a data file containing a result of that gradient analysis.

3. A non-transitory computer readable media recording a program for making a computer function as the analysis controller and the preparatory liquid supply controller according to claim 1.

4. A control apparatus for controlling an operation of a liquid chromatograph that has a gradient analysis function in which a chromatograph analysis is performed while a mixture ratio of a plurality of solvents composing a mobile phase is temporally changed, the control apparatus comprising:
   a) an analysis controller programmed to control the liquid chromatograph so as to change the mixture ratio of the solvents when performing a sample analysis, from a first mixture ratio, in which an elution capability of the mobile phase is lowest in the sample analysis, to a second mixture ratio, in which the elution capability of the mobile phase is highest in the sample analysis, and then again to the first mixture ratio, the first mixture ratio and the second mixture ratio being defined by a user; and b) a preparatory liquid supply controller programmed to control the liquid chromatograph so as to perform, before the sample analysis, a preparatory liquid supply in which the mixture ratio of the solvents is changed from the first mixture ratio, which is a same as in the sample analysis, to the second mixture ratio, which is a same as in the sample analysis, and then again to the first mixture ratio, wherein:

if a plurality of sample analyses are performed and if a kind of column, kinds of solvents, the first mixture ratio, and the second mixture ratio used in two successively performed sample analyses are a same, the preparatory liquid supply controller is programmed to omit the preparatory liquid supply between the two sample analyses, and if at least one of the kind of column, kinds of solvents, the first mixture ratio, and the second mixture ratio used in two successively performed sample analyses is not the same, the preparatory liquid supply controller is programmed to perform the preparatory liquid supply between the two sample analyses in a manner so that a time required to perform the preparatory liquid supply before the sample analysis is reduced with respect to a time required to perform the sample analysis.

5. The control apparatus for a liquid chromatograph according to claim 4, further comprising:

c) an analysis result storing unit programmed to store each result of multiple gradient analyses in one data file; and d) an automatic data file naming unit programmed to assign a file name which includes at least one of either a column name or names of the solvents used in each of the gradient analyses, a mixture ratio of the solvents at a point of initiation of a process of continuously changing the mixture ratio of the solvents in each of the gradient analyses, or a mixture ratio of the solvents at a point of termination of that process in each of the gradient analyses, to a data file containing a result of that gradient analysis.

6. A non-transitory computer readable media recording a program for making a computer function as the analysis controller and the preparatory liquid supply controller according to claim 4.

7. The control apparatus for a liquid chromatograph according to claim 4, further comprising:

c) an analysis result storing unit programmed to store each result of multiple gradient analyses in one data file; and d) an automatic data file naming unit programmed to assign a file name which includes at least a column name used in each of the gradient analyses to a data file containing a result of that gradient analysis.

8. The control apparatus for a liquid chromatograph according to claim 1, wherein all conditions other than the rate at which the mixture ratio of the solvents is continuously changed from the initial mixture ratio to the final mixture ratio are the same between the sample analysis and the preparatory liquid supply.

9. The control apparatus for a liquid chromatograph according to claim 1, wherein:

the analysis controller and the preparatory liquid supply controller are programmed to perform, when performing the sample analysis and the preparatory liquid supply, respectively, a gradient process in which the mixture ratio of the solvents is continuously changed from the initial mixture ratio to the final mixture ratio, a washing process in which an inside of a column of the liquid chromatograph is washed after the gradient process, and an equilibration process in which the inside of the column of the liquid chromatograph is equilibrated after the washing process, the analysis controller is programmed to control the liquid chromatograph so as to perform, when performing the sample analysis, the gradient process in which the mixture ratio of the solvents is continuously changed from the initial mixture ratio to the final mixture ratio, the preparatory liquid supply controller is programmed to perform, when performing the preparatory liquid supply, the gradient process in which the mixture ratio of the solvents is continuously changed from the initial mixture ratio to the final mixture ratio, the preparatory liquid supply controller is programmed to perform the gradient process at the rate higher than the analysis controller, and each of the analysis controller and the preparatory liquid supply controller is programmed to perform the washing process and the equilibration process at a same rate.

* * * * *